United States Patent
Neroev et al.

(10) Patent No.: US 8,894,560 B2
(45) Date of Patent: Nov. 25, 2014

(54) METHOD FOR PREVENTING THE ONSET AND PROGRESSION OF MYOPIA

(71) Applicants: The Helmholtz Moscow Research Institute of Eye Diseases, Moscow (RU); Vladimir V. Neroev, Moscow (RU); Elena P. Tarutta, Moscow (RU); Natalya A. Tarasova, Ramenskoe (RU); Sergey M. Shakhray, Moscow (RU)

(72) Inventors: Vladimir V. Neroev, Moscow (RU); Elena P. Tarutta, Moscow (RU); Natalya A. Tarasova, Ramenskoe (RU); Sergey M. Shakhray, Moscow (RU)

(73) Assignees: The Helmholtz Moscow Research Institute of Eye Diseases, Moscow (RU); Vladimir V. Neroev, Moscow (RU); Elena P. Tarutta, Moscow (RU); Natalya A. Tarasova, Ramenskoe, Moskovskaya Obl. (RU); Sergey M. Shakhray, Moscow (RU)

( * ) Notice: Subject to any disclaimer, the term of this patent is extended or adjusted under 35 U.S.C. 154(b) by 0 days.

(21) Appl. No.: 14/270,027

(22) Filed: May 5, 2014

(65) Prior Publication Data

US 2014/0243583 A1     Aug. 28, 2014

Related U.S. Application Data

(63) Continuation of application No. PCT/RU2012/000476, filed on Jun. 19, 2012.

(30) Foreign Application Priority Data

Nov. 11, 2011   (RU) ................................ 2011145682

(51) Int. Cl.

| | |
|---|---|
| *A61N 2/00* | (2006.01) |
| *A63B 49/00* | (2006.01) |
| *A61H 5/00* | (2006.01) |
| *A61N 5/06* | (2006.01) |
| A61N 5/067 | (2006.01) |
| A63B 67/18 | (2006.01) |

(52) U.S. Cl.
CPC *A61N 2/002* (2013.01); *A61H 5/00* (2013.01); *A61N 5/0616* (2013.01); *A61N 2/004* (2013.01); *A63B 49/00* (2013.01); *A61N 2005/067* (2013.01); *A63B 67/18* (2013.01); *A63B 2243/0087* (2013.01)
USPC .................................. 600/9; 607/89; 128/898

(58) Field of Classification Search
USPC .............. 128/898; 606/2, 4, 13; 607/1, 88, 89
See application file for complete search history.

(56) References Cited

FOREIGN PATENT DOCUMENTS

| | | |
|---|---|---|
| RU | 2284175 C2 | 11/2003 |
| RU | 2242208 C2 | 12/2004 |
| SU | 921561 | 4/1982 |

OTHER PUBLICATIONS

International Search Report from International Application No. PCT/RU2012/000476 filed Jun. 19, 2012, mailed Oct. 4, 2012.
Tarutta, E. P, et al, Medical Technology: "Integrated Non-Surgical Treatment of Progressive Myopia," FSI "Helmholtz Moscow Research Institute of Eye Diseases, Ministry of Healthcare and Social Development of the Russian Federation," 2010, Moscow.
Livado, E.I., Exercise Therapy in Combination Treatment of Myopia in Children. Author Abstract of Ph.D. Thesis in Medical Science, 1977 Moscow.
Stishkovskaya, N. N., Complex Method for Improving Eye Hemodynamics Parameters of Patients with Myopia, Author Abstract of Ph.D. Thesis in Medical Science, 1979, Moscow.
Medvedskaya, G. A., Prevention of Myopia and Its Progression through the Influence on Accommodative Apparatus of Eye. Author Abstract of Ph.D. Thesis in Medical Science, 1981, Kalinin.
Neroev, V. V. et al, "Reflex Therapy, Massage, and Manual Therapy in the Treatment of Progressive Myopia in Children and Adolescents," Vestnik Oftalmologii, Jul.-Aug. 2006—122(4), c. 20-24, abstract.

*Primary Examiner* — Samuel Gilbert
(74) *Attorney, Agent, or Firm* — Patentbar International, P.C.

(57) ABSTRACT

The present invention relates to ophthalmology, and is designated to prevent onset and progression of myopia. The treatment course, including eye exposure with magnetic field, transscleral low-energy laser radiation with wavelength of 1.3 microns, and additional optical—reflectory eye trainings, is conducted. The entire treatment course is 5 procedures every other day. initial badminton trainings are performed for 2 months three times a week for 2 hours. During the treatment course trainings are performed 2 times a week on days free of the treatment. On completing the treatment course trainings are performed 2-3 times a week for 1 year. The method makes it possible to reduce the length of the treatment and decrease the number of procedures—sessions of functional treatment of myopia with increasing and prolonging efficiency of prevention and treatment of myopia with increasing positive psychological attitude to the treatment of child.

1 Claim, No Drawings

METHOD FOR PREVENTING THE ONSET AND PROGRESSION OF MYOPIA

RELATED APPLICATIONS

This Application is a Continuation application of International Application PCT/RU2012/000476, filed on Jun. 19, 2012, which in turn claims priority to Russian Patent Applications No. RU 2011145682, filed Nov. 11, 2011, both of which are incorporated herein by reference in their entirety.

FIELD OF THE INVENTION

The present invention relates to ophthalmology, and is intended to prevent onset and progression of myopia.

In accordance with the three-factor theory of acquired myopia pathogenesis, reduction of accommodative ability of eyes plays a leading role in the onset and progression of myopia. Disorders of the accommodative ability are associated (apart from genetic predisposition) with the reduction of local and cerebral hemodynamics, physical inactivity, general medical conditions, immune disorders. Physical activity limitation of people with myopia, as it has been recommended just a while ago, was recognized as invalid. The important role of physical trainings in the prevention of myopia and its progression was shown, since physical exercises contribute to the overall strengthening of the organism, enhancement of its functions, and also improve efficiency of ciliary muscle and promote scleral coat of eye.

BACKGROUND OF THE INVENTION

In recent decades, many studies were conducted. These studies showed that performance efficiency enhancement of eye accommodative apparatus by use of special exercises and normalization of blood supply of the eye tissues lead to inhibition of the myopia progression, and sometimes prevent its onset (Medvedskaya G A Prevention of myopia and its progression through the influence on accommodative apparatus of eye. Author abstract of Ph.D. thesis in Medical Science. Kalinin, 1981; Stishkovskaya N N Complex method for improving eye hemodynamics parameters of patients with myopia. Author abstract of Ph.D. thesis in Medical Science. Moscow, 1979). Studies of E. I. Livado (Livado E I Exercise therapy in combination treatment of myopia in children. Author abstract of Ph.D. thesis in Medical Science. Moscow, 1977) revealed that the decrease in overall physical activity of pupil under a high optical burden may result in the development of myopia. On the basis of the results of conducted studies a methodology of the exercise therapy for pupils with myopia was developed, and its efficiency when using in a set of measures for the prevention and progression of myopia was shown.

It is known the use of the following treatment complex for the prevention of onset and progression of myopia: 10 procedures of low-energy transscleral laser stimulation of ciliary body in conjunction with a course of instillation or bath magnetophoresis with 4% taufon solution. The procedure for transscleral laser stimulation of ciliary body involves the use of, for example, device MAKDEL 00.00.09, in a form of special spectacles that provide infrared rays with a wavelength of $\lambda=1.3$ nm in the ciliary zone. For maximum effect, 2 and 3 modes of output power (1.0-1.5 mW) for 2-3 minutes are used. The course consists of 8-10 procedures once or twice a day (in the latter case with 30-40 minute break). Magnetophoresis is conducted using low-intensity (voltage of about 10 mT) alternating 50-cycle magnetic field with a pulse repetition frequency of 12.5 Hz and reversal time of 10 second, in particular, the magnetic field is induced by the device for magnetotherapy "Polus-3." Exposure time is 10 minutes. The course of the treatment consists of 10 procedures which are accomplished daily. In this case, positive effects of both factors—the magnetic field and drug preparation can be summarized in one procedure (Medical Technology: "Integrated non-surgical treatment of progressive myopia," FSI "Helmholtz Moscow Research Institute of Eye Diseases, Ministry of Healthcare and Social Development of the Russian Federation, Moscow, 2010, www.promed.ru). This method was chosen as the closest analogous solution. However, this method is not effective enough, because 3 months after the treatment effect achieved begins to decrease, and 6 months after the treatment has to be repeated. In addition, magnetophoresis comprises instillation of 4% taufon solution, this procedure is often accompanied by pain and redness, and this, in its turn, reduces the positive psychological attitude for treatment of the child. Furthermore, this method mainly improves local circulation, does not affect the cerebral hemodynamics and does not substantially increase the accommodative ability of eyes.

Beneficial effects of different optical—reflectory manipulations on the dynamic refraction and rate of myopia progression are known, so in order to enhance the effect of the chosen procedures, we included optical—reflectory exercises that can be done, for example, on ophthalmomyotraining device "Vizotronik", into the treatment measures.

Badminton is a sport which harmoniously combines keeping track of a moving object (accommodation training), turns of head and body (increasing total and cerebral circulation), deep breathing (oxygenation of blood).

SUMMARY OF THE INVENTION

Objective of the study is the development of more effective complex method for the prevention and progression of myopia.

The technical result of the proposed method is the possibility to reduce the length of treatment and to decrease the number of procedures (sessions for the treatment of functional myopia) with increased and prolonged efficiency of the prophylaxis and treatment of myopia associated with positive psychological attitude for treatment in a child.

The technical result is achieved by means of integrated influence of four different factors—laser, magnetic, optical—reflectory impacts affecting in a certain mode on the different elements of pathogenesis of myopia development and progression, combined with badminton trainings in a certain mode before, during and after the course of the functional treatment of myopia.

Badminton trainings without combination with other therapeutic measures resulted in stabilization of refraction, increasing reserves of relative accommodation by 25%, increasing reserves of absolute accommodation by 47% and objective accommodative response by 9%. Hemodynamics indices in the ophthalmic artery were improved by 3%, in the lateral posterior short ciliary arteries—by 21%, in the medial posterior short ciliary arteries—by 14%, in the central retinal vein—by 17%. After 6 months the indices of refraction, accommodation and hemodynamics were decreased slightly and were 9-15% higher than initial level. This allows to replace magnetophoresis using 4% taufon solution with magnetic effect of alternating magnetic field and avoid soreness and eyes redness, halve the number of procedures that facilitates the treatment regimen for patients.

We conducted investigations of refraction, accommodation and hemodynamics in 3 groups of patients.

Group 1 consisted of 20 patients who received only badminton trainings 3-4 times a week for 2 hours a day over a period of 2 months.

Group 2 consisted of 20 patients that were treated with 10 procedures of the transscleral low-energy laser stimulation of ciliary body in conjunction with a course of instillation or bath magnetophoresis with 4% taufon solution and optical—reflectory trainings on ophthalmomyotraining device—relaxation oscillator "Vizotronik."

Group 3 consisted of 20 patients who received badminton trainings over a period of 2 months 3 times a week for 2 hours a day, and then they were treated with a course of magnetotherapy with alternating magnetic field without taufon instillations combined with transscleral laser stimulation of ciliary body and optical—reflectory trainings (5 procedures every other day), in the days free of the treatment they had badminton trainings 2 times a week. On completing the treatment course they had badminton trainings 2-3 times a week over a period of 1 year.

In group 1 reserves of the relative accommodation were increased by 25%, the absolute accommodation—by 47%, the objective accommodative response—by 9%. Hemodynamics indices in the ophthalmic artery were improved by 3%, in the lateral posterior short ciliary arteries—by 21%, in the medial posterior short ciliary arteries—by 14%, in the central retinal vein—by 17%. After 6 months, indices of refraction, accommodation and hemodynamics were decreased slightly and were 9-15% higher than initial level.

In group 2 reserves of the relative accommodation were increased by 15%, the absolute accommodation—by 28%, the objective accommodative response was not changed. Hemodynamics indices in the ophthalmic artery were improved by 5%, in the lateral posterior short ciliary arteries—by 25%, in the medial posterior short ciliary arteries—by 15%, in the central retinal vein—by 20%. After 6 months, indices of refraction, accommodation and hemodynamics were decreased almost to the original level.

In group 3 reserves of relative accommodation were increased by 35%, the absolute accommodation—by 54%, the objective accommodative response—by 15%. Hemodynamics indices in the ophthalmic artery were improved by 10%, in the lateral posterior short ciliary arteries—by 35%, in the medial posterior short ciliary arteries—by 25%, in the central retinal vein—by 25%. After 6 and 12 months indices of refraction, accommodation and hemodynamics were stable and remained at the attained level.

Thus, in group 3, where combined remedial and prophylactic action was presented, there was the highest and the most stable increase of the relative and absolute accommodation, objective accommodative response and hemodynamics, at that, the length of treatment was reduced, and the negative factor of subjective effects in a form of topical administration of taufon was eliminated.

The method is accomplished as follows. At first, badminton trainings are performed for 2 months (3 trainings per week for 2 hours). Then, a set of functional treatment: one day—magnetotherapy with low intensity alternating magnetic field induced, for example, by an apparatus for magnetotherapy "Polus-3" for 10 minutes, low-energy laser stimulation of the ciliary body, for example, using device "MACDEL 09" for 2-3 min, optical and reflex training of eyes, for example, using ophthalmomyotraining device—relaxation oscillator "Vizotronik" in accordance with method No. 1, is accomplished. Treatment course is 5 procedures in every other day. Sequence of functional treatment procedures is not essential.

Badminton trainings are performed in days free of the treatment, 2 times a week. After the functional treatment badminton trainings are continued 2-3 times a week for 1 year.

EXAMPLE 1

Patient D., 11 years old. Diagnosis: medium severity myopia, slowly progressive. Refraction before trainings was −4.09 diopters, relative accommodation reserves (RAR)=0.5 diopters, absolute accommodation value (AAV)=5.5 diopters, objective accommodative response (OAR)=−1.25 diopters. Hemodynamics indices were reduced in comparison with age-norm in all vessels of eyeball. After 2 months of badminton trainings, three times a week for 2 hours, refraction was almost unchanged and had the value—4.08 diopters, RAR=0.75 diopters, AAV=8.0 diopters, OAR=−1.5 diopters, hemodynamic parameters in ophthalmic arteries were improved by 3%, in the lateral posterior short ciliary arteries—by 21%, in the medial posterior short ciliary arteries from 7 to 15%, in the central retinal vein by—18%. After the treatment course, comprising the use of magnetotherapy of low intensity (about 10 mT) 50-cycle alternating magnetic field with pulse repetition frequency of 12.5 Hz and reversal time 10 s. in combination with transscleral laser stimulation of ciliary body using apparatus "MACDEL 09" with 2 and 3 modes of radiation (1.0-1.5 mW) for 2-3 min and optical—reflectory trainings on ophthalmomyotraining device—relaxation oscillator "Vizotronik" for 5 days in every other day, as well as badminton trainings two times a week in free of the treatment days, refraction was decreased by 0.1 diopters, RAR was increased by 0.25 diopters and had the value of 1.0 diopters, AAV was increased by 0.75 diopters and had the value of 8.75 diopters, OAR was increased and amounted to −1 72 diopters. Hemodynamics indices in ophthalmic artery were improved by 10%, in lateral posterior short ciliary arteries—by 35%, in medial posterior short ciliary arteries—by 26%, in the central retinal vein—by 26%. On completing treatment course, badminton trainings were performed 2-3 times a week for 1 year.

After 6 and 12 months indices of refraction, accommodation and hemodynamics were stable and remained at the attained level.

EXAMPLE 2

Patient Z., 11 years old. Diagnosis: pseudomyopia, family history of myopia. Before trainings refraction for constricted pupil was—1.09 diopters, after cycloplegia—emmetropy. Relative accommodation reserves (RAR) were reduced=1.5 diopters, absolute accommodation value (AAV)=6.5 diopters, objective accommodative response (OAR)=−1.75 diopters. Hemodynamics indices were reduced in comparison with age-norm in all vessels of eyeball. After 2 months of badminton trainings noncycloplegic refraction was almost unchanged and had the value −1.08 diopters, RAR=2.0 diopters, AAV=9.5 diopters, OAR=−1.72 diopters, hemodynamic parameters in ophthalmic artery was improved by 4%, in lateral posterior short ciliary arteries—by 22%, in medial posterior short ciliary arteries—by 16%, in central retinal vein—by 20%. After the course of non-surgical treatment, comprising the use of magnetotherapy with low intensity (about 10 mT) 50-cycle alternating magnetic field with pulse repetition frequency of 12.5 Hz and reversal time 10 s. in combination with transscleral laser stimulation of ciliary body using apparatus "MACDEL 09" with 2 and 3 modes of radiation (1.0-1.5 mW) for 2-3 min and optical—reflectory trainings on ophthalmomyotraining device—relaxation oscillator "Vizotronik" for 5 days in every other day, as well as badminton trainings two times a week in free of the treatment days, noncycloplegic refraction was dropped to the value of effetropy, RAR was increased by 0.25 diopters and had the value of 2.25 diopters, AAV was increased by 0.5 diopters and had the value of 10.0 diopters, OAR was 1.87 diopters. Thus, elimination of habitual excessive accommodation tonus (HEAT) was shown. Hemodynamics indices in ophthalmic artery were improved by 10%, in lateral posterior short ciliary arteries—by 35%, in medial posterior short ciliary arteries—by 26%, in central retinal vein—by 26%. After the treatment badminton trainings were performed 2-3 times a week for 1 year.

After 6 and 12 months indices of cycloplegic refraction, accommodation and hemodynamics were stable and remained at the attained level.

Thus, the proposed method for the prophylaxis and treatment of progressive myopia can increase and prolong the therapeutic effect by improving accommodation, local and cerebral hemodynamics, reducing the number of visits with increasing positive psychological attitude to the treatment of child.

What is claimed is:

1. A method for preventing myopia onset and progression in a person, comprising the steps of:

performing badminton trainings for the person for 2 months three times a week for 2 hours followed by a treatment course of combined eye exposure with magnetic field and transscleral low-energy laser radiation with wavelength of 1.3 microns, wherein the treatment course includes 5 combined eye exposure procedures, wherein one of the combined procedures is conducted every other day, and wherein each combined procedure is followed on the same day by an optical—reflectory eye training;

performing badminton trainings during the treatment course twice a week in days free from the combined procedure; and performing badminton trainings on completing the treatment course 2-3 times a week for 1 year.

* * * * *